US012685521B2

(12) United States Patent
Bohl

(10) Patent No.: US 12,685,521 B2
(45) Date of Patent: Jul. 21, 2026

(54) SYSTEMS AND METHODS FOR SPINAL REALIGNMENT

(71) Applicant: Dignity Health, San Francisco, CA (US)

(72) Inventor: Michael Bohl, San Francisco, CA (US)

(73) Assignee: Dignity Health, San Francisco, CA (US)

( * ) Notice: Subject to any disclaimer, the term of this patent is extended or adjusted under 35 U.S.C. 154(b) by 485 days.

(21) Appl. No.: 17/998,480

(22) PCT Filed: May 14, 2020

(86) PCT No.: PCT/US2020/032845
§ 371 (c)(1),
(2) Date: Nov. 10, 2022

(87) PCT Pub. No.: WO2021/230871
PCT Pub. Date: Nov. 18, 2021

(65) Prior Publication Data
US 2023/0200795 A1 Jun. 29, 2023

(51) Int. Cl.
*A61B 17/02* (2006.01)
*A61B 17/00* (2006.01)
*A61B 17/56* (2006.01)

(52) U.S. Cl.
CPC .... *A61B 17/025* (2013.01); *A61B 2017/0046* (2013.01); *A61B 2017/0256* (2013.01); *A61B 2017/564* (2013.01)

(58) Field of Classification Search
CPC .......... A61B 17/025; A61B 2017/0046; A61B 2017/0256; A61B 2017/564; A61B 17/56
See application file for complete search history.

(56) References Cited

U.S. PATENT DOCUMENTS

| | | | | |
|---|---|---|---|---|
| 8,123,807 B2 * | 2/2012 | Kim | .................. | A61B 17/7065 |
| | | | | 623/17.15 |
| 9,198,698 B1 | 12/2015 | Doose et al. | | |
| 10,159,583 B2 * | 12/2018 | Dietzel | ................ | A61F 2/4657 |
| 11,992,410 B1 * | 5/2024 | Moseley | ........... | A61B 17/8645 |
| 2007/0185490 A1 * | 8/2007 | Implicito | ............. | A61B 17/025 |
| | | | | 606/249 |
| 2008/0071380 A1 | 3/2008 | Sweeney | | |
| 2009/0054988 A1 * | 2/2009 | Hess | .................. | A61B 17/025 |
| | | | | 623/17.11 |
| 2013/0237766 A1 * | 9/2013 | Pell | ................. | A61B 17/12136 |
| | | | | 600/211 |
| 2013/0325128 A1 | 12/2013 | Perloff et al. | | |
| 2015/0305785 A1 | 10/2015 | Taber et al. | | |
| 2018/0273359 A1 * | 9/2018 | Cheung | .................... | B66F 3/12 |

OTHER PUBLICATIONS

Patent Cooperation Treaty, International Search Report and Written Opinion, International Application No. PCT/US2020/032845, date of Mailing Oct. 6, 2020, 11 pages.

* cited by examiner

*Primary Examiner* — Eduardo C Robert
*Assistant Examiner* — Holly Joanna Lane
(74) *Attorney, Agent, or Firm* — Polsinelli PC

(57) ABSTRACT

Various embodiments of an anchor and intradiscal implant for surgical realignment of a misaligned spine are disclosed herein.

16 Claims, 13 Drawing Sheets

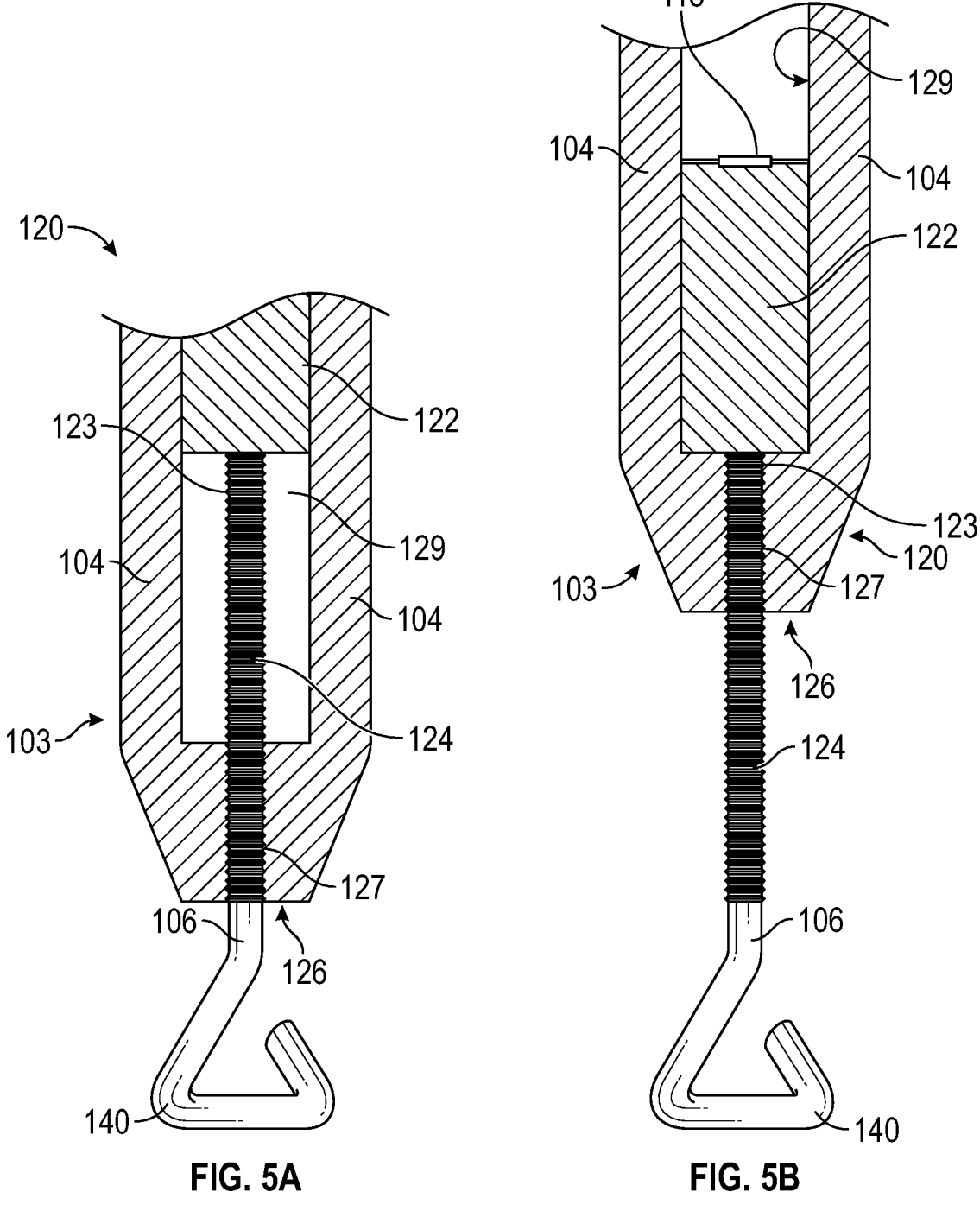
FIG. 5A                    FIG. 5B

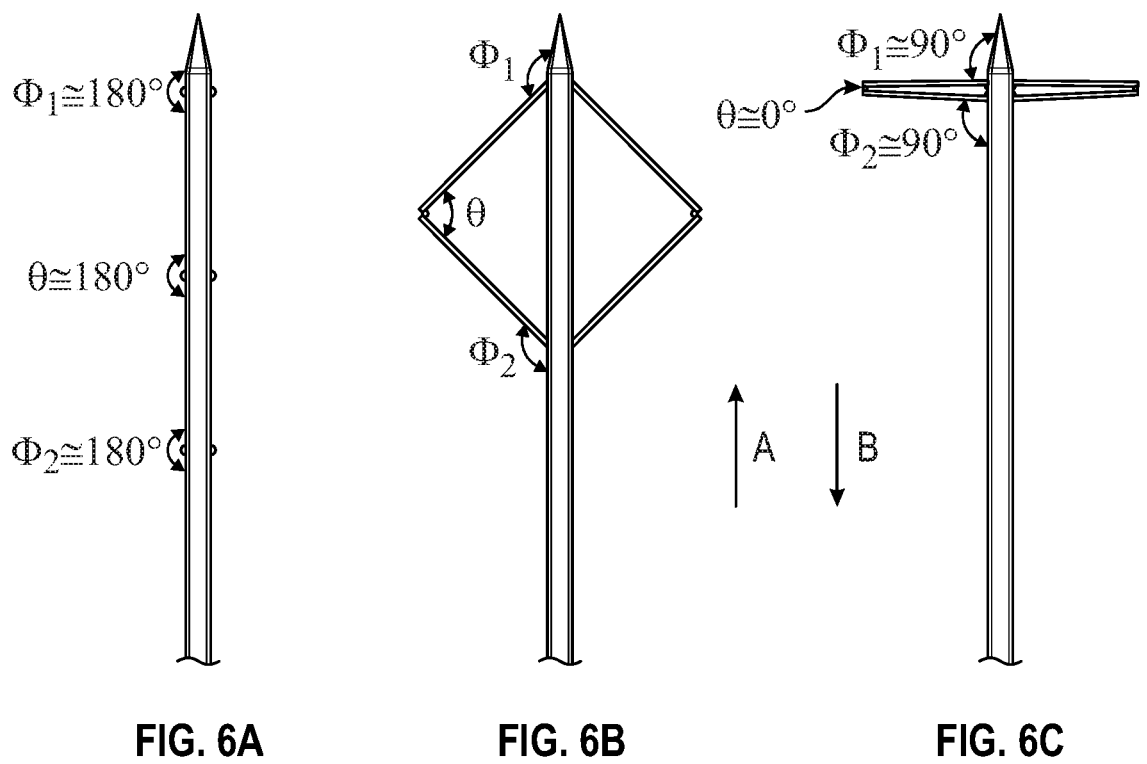
FIG. 6A                    FIG. 6B                    FIG. 6C

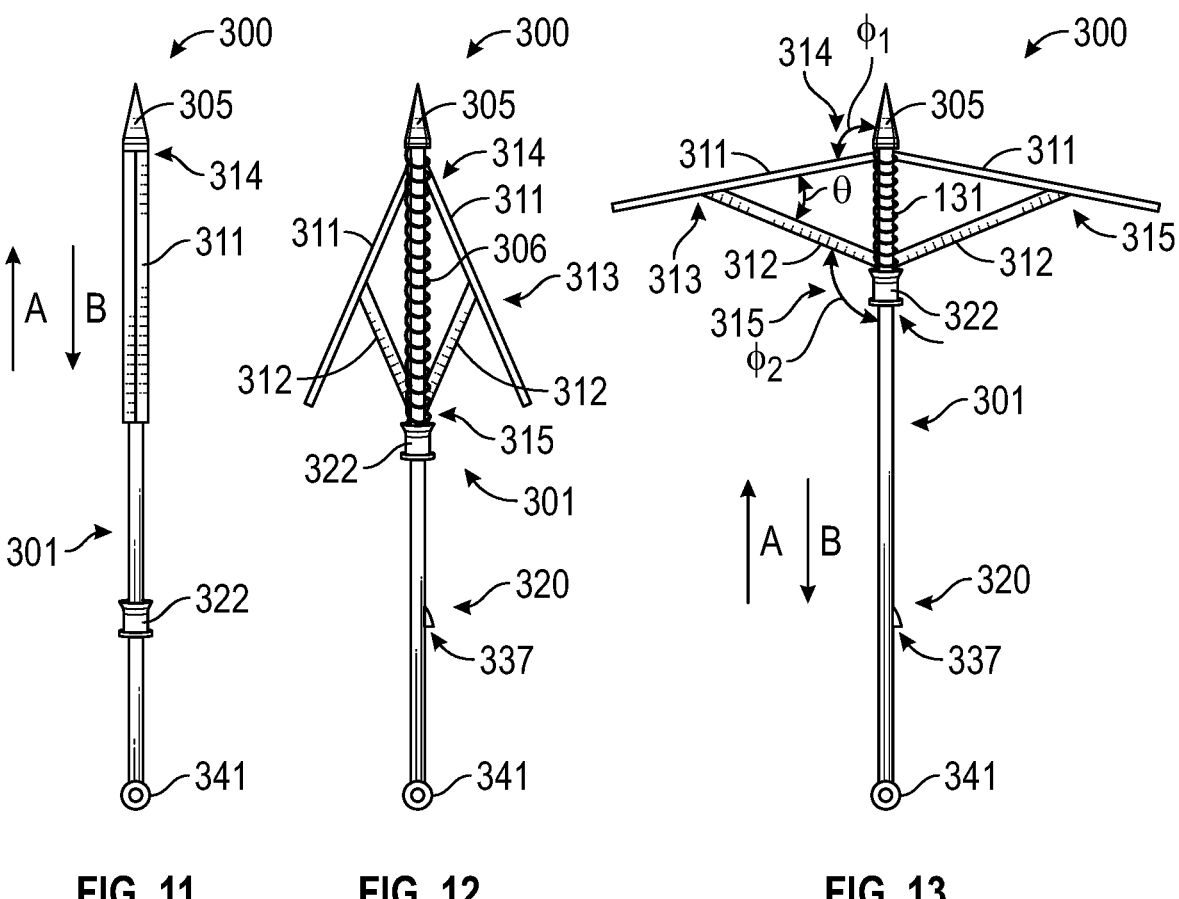
FIG. 11      FIG. 12      FIG. 13

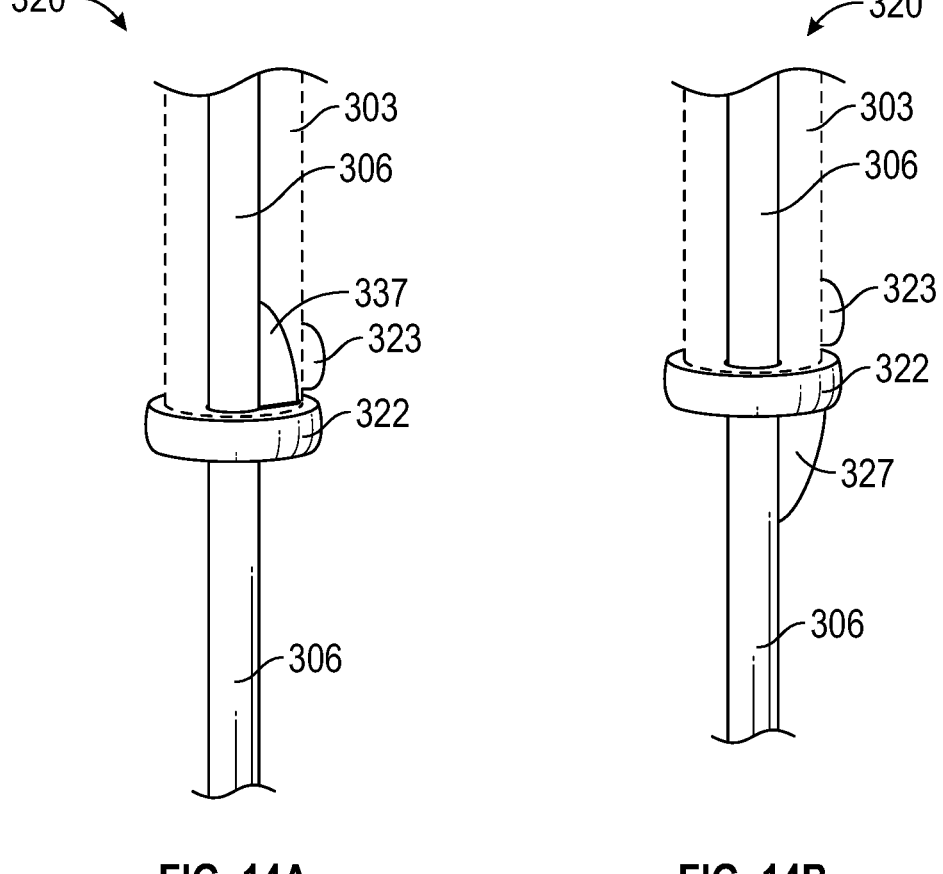
FIG. 14A                    FIG. 14B

400/500

400/500

100/200/
300

SYSTEMS AND METHODS FOR SPINAL REALIGNMENT

FIELD

The present disclosure generally relates to medical apparatuses and devices, and in particular, to a surgical apparatus for realignment of a misaligned spine during spinal realignment surgery.

BACKGROUND

The surgical correction of a misaligned spine often requires realignment in three different planes: sagittal, coronal, and axial. Examples of current spinal reconstruction techniques include anterior column release (through an anterior or lateral approach), discectomy and placement of inter-body grafts, pedicle screw fixation, cantilever rod bending, axial de-rotation maneuvers, and differential rod bending. The majority of corrective force applied to the spine using these maneuvers is applied to the posterior column of the spine via pedicle screws. Laterally applied forces to pedicle screws can risk pedicle screw failure and pedicle fracture, thereby limiting the amount of axial and coronal correction achievable.

It is with these observations in mind, among others, that various aspects of the present disclosure were conceived and developed.

BRIEF DESCRIPTION OF THE DRAWINGS

FIGS. 5A-5B are frontal views of a locking mechanism of the anchor apparatus of FIG. 1 showing a lifting block in the "deployed" position and the "non-deployed" position, respectively;

FIGS. 6A-6C are frontal views of the anchor apparatus of FIG. 1 illustrating angles $\phi_1$, $\theta$, and $\phi_2$ in the "non-deployed", "deploying" and "deployed" positions respectively;

FIG. 11 is a frontal view of a third embodiment of the anchor apparatus for realignment of a misaligned spine in a "non-deployed" position;

FIG. 12 is a frontal view of the anchor apparatus of FIG. 11 for realignment of a misaligned spine in a "deploying" position;

FIG. 13 is a frontal view of the anchor apparatus of FIG. 11 for realignment of a misaligned spine in a "deployed" position;

FIGS. 14A-14B are frontal views of a locking mechanism of the anchor apparatus of FIG. 11 showing a runner in engagement with a lower fin in the "non-deployed" position and the runner in engagement with an upper fin in the "deployed" position;

Corresponding reference characters indicate corresponding elements among the view of the drawings. The headings used in the figures do not limit the scope of the claims.

DETAILED DESCRIPTION

Figures 1, 2, 3:
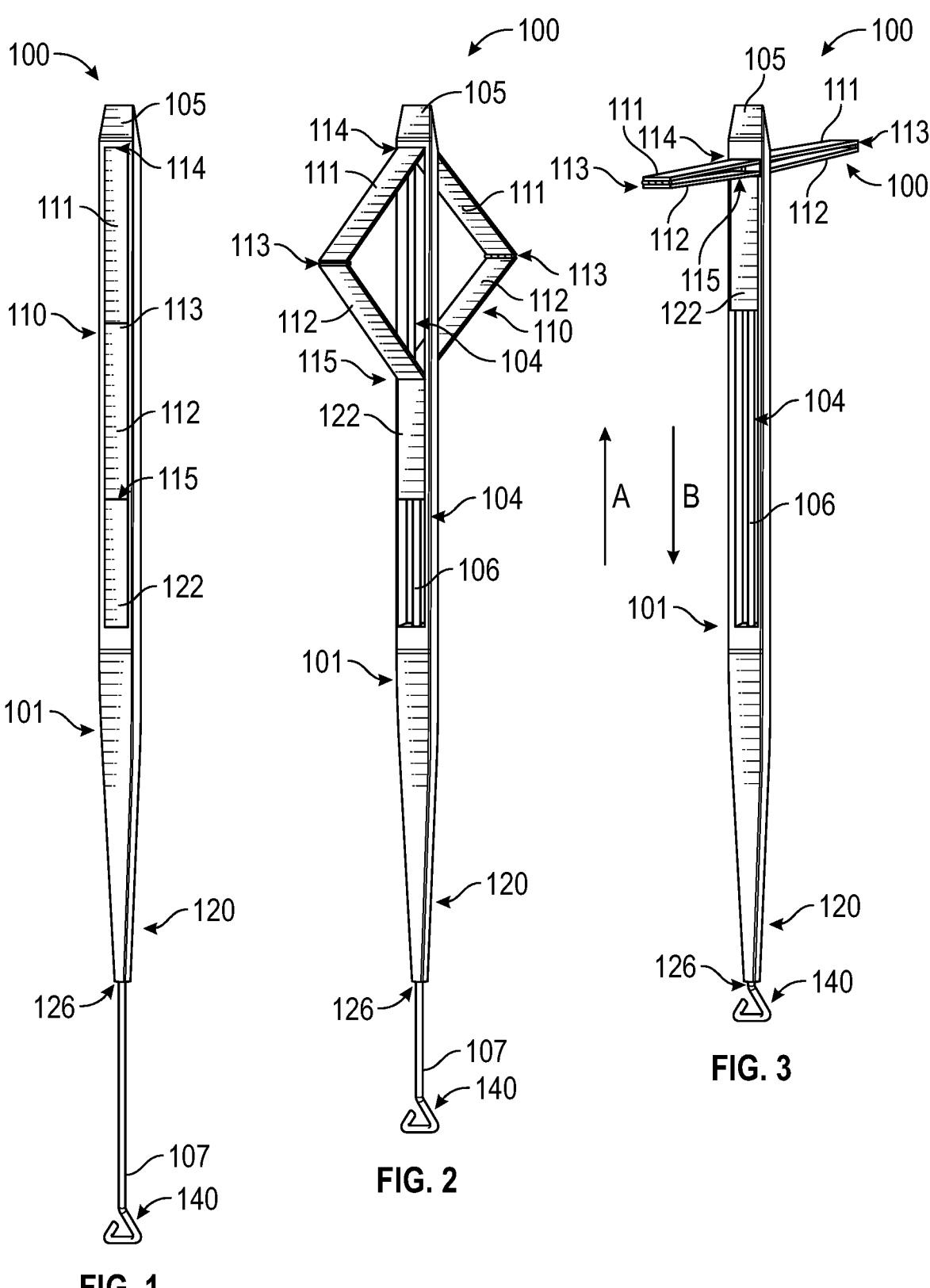
FIG. 1 is a perspective view of a first embodiment of an anchor apparatus for realignment of a misaligned spine in a "non-deployed" position.
FIG. 2 is a perspective view of the anchor apparatus of FIG. 1 for realignment of a misaligned spine in a "deploying" position.
FIG. 3 is a perspective view of the anchor apparatus of FIG. 1 for realignment of a misaligned spine in a "deployed" position.

The present disclosure relates to an anchor apparatus and associated devices for surgical realignment of a misaligned spine. More specifically, the anchor apparatus includes an elongated body defining an upper section and a lower section, a pair of foldable wings extending from the elongated body and a locking mechanism such that a user can insert the anchor apparatus between two vertebrae in a first axial direction, deploy the wings, and pull on the anchor apparatus in an opposite second axial direction to force the misaligned spine into realignment. In some embodiments, the anchor apparatus may require an intradiscal implant having a channel to aid with the insertion of the anchor apparatus between vertebrae. Referring to the drawings, embodiments of the anchor apparatus are illustrated and generally indicated as 100 in FIGS. 1-6, 200 in FIGS. 7-10, and 300 in FIGS. 11-14 and embodiments of the intradiscal implant are illustrated and generally indicated as 400 and 500 in FIGS. 15 and 16.

As shown in FIGS. 1-6, in some embodiments the anchor apparatus 100 includes an elongated body 101 defining an upper section 102 and a lower section 103 with the upper portion 102 defining a head 105 and a pair of foldable wings 110 that are deployed by driving a lifting block 122 defined by the lower portion 103 of the elongated body 101 along an axial direction A such that the foldable wings 110 of the elongated body 101 collapse into an "anchor" shape. The anchor apparatus 100 further includes an inner rod 106 for driving the lifting block 122 in the first axial direction A or an opposite second axial direction B such that the anchor apparatus 100 can be locked in a "non-deployed" position (FIGS. 1 and 4A) or a "deployed" position (FIGS. 3 and 4C). An intermediate "deploying" position is illustrated in FIGS.

2 and 4B. In the deployed position, a lateral extension profile of the anchor apparatus 100 is expanded. Conversely, in the non-deployed position, the lateral extension profile of the anchor apparatus 100 is minimized.

In some embodiments, the elongated body 101 forms a generally square rod shape defining the upper section 102 and the lower section 103. As discussed above, the elongated body 101 further defines the pair of foldable wings 110 which, when in the "non-deployed" position, form part of the upper section 102 of the elongated body 101. The elongated body 101 further defines a channel 104 defining a pair of tracks 104A and 104B. Each track 104A and 104B is located along a lateral side of the elongated body 101 and extends in a longitudinal direction. Each track 104A and 104B is configured to receive the lifting block 122 such that the lifting block 122 is operable to be driven through the channel 104 along the tracks 104A and 104B in a first axial direction A or an opposite second axial direction B. In some embodiments, the tracks 104 include a grooved surface 129 to aid with the engagement of the tracks 104 with the lifting block 122.

In some embodiments of the anchor apparatus 100, each of the pair of foldable wings 110 form part of the upper section 102 of the elongated body 101. Each of the pair of foldable wings 110 defines an upper wing portion 111 and a lower wing portion 112, wherein a proximal end of the upper wing portion 111 and a distal end of the lower wing portion 112 are joined through a middle joint 113. As shown in FIGS. 6A-6C, the middle joint 113 allows one rotational degree of freedom and defines a main angle $\theta$ between the upper wing portion 111 and the lower wing portion 112. The upper wing portion 111 is joined to the head 105 of the elongated body 101 by an upper joint 114. The upper joint 114 similarly allows one rotational degree of freedom to define an upper angle $\phi_1$ between the upper wing portion 111 of the foldable wing 110 and the head 105 of the elongated body 101. The lower wing portion 112 is joined to an upper surface of the lifting block 122 of the elongated body 101 by a lower joint 115. The lower joint 115 allows one rotational degree of freedom to define a lower angle $\phi_2$ between the lower wing portion 112 of the foldable wing 110 and lifting block 122 of the elongated body 110. As shown in FIG. 6A, while in the non-deployed position, all three angles $\phi_1$, $\theta$, and $\phi_2$ are about 180°. Conversely, as shown in FIG. 6C, while in the deployed position, the upper and lower angles $\phi_1$, and $\phi_2$ are about 90° and the main angle $\theta$ is close to 0°. A view of the angles $\phi_1$, $\theta$, and $\phi_2$ in the intermediate "deploying" position is shown in FIG. 6B.

A locking mechanism 120 of the anchor apparatus 100 is shown in FIGS. 5A-5B. In some embodiments, the lower section 103 and channel 104 of the elongated body 101 collectively define a terminal end 126. The terminal end 126 further includes an inner threading 127 for engagement with the inner rod 106. As shown in FIGS. 5A-5B, the inner rod 106 includes a threaded portion 124 and is operably connected with the lifting block 122 such that when the inner rod 106 is rotated in a first clockwise or counterclockwise direction Q or an opposite second clockwise or counterclockwise direction R within the inner threading 127 of the tapered terminal end 126 causes the lifting block 122 to be driven in the first axial direction A or driven in the opposite second axial direction B. In some embodiments, an upper end 123 of the inner rod 106 is engaged with a receptacle (not shown) defined along a bottom surface of the lifting block 122 such that the inner rod 106 is operable for free rotation within the receptacle of the lifting block 122 and the lifting block 122 follows vertical motion of the inner rod 106.

The collapsibility of the pair of foldable wings 110 into a folded configuration is made possible by the operative co-operation of the lifting block 122 and the inner rod 106. As discussed above, the inner rod 106 is disposed through the lower section 103 of the elongated body 101 such that the inner rod 106 attaches at the lower surface of the lifting block 122 and extends out of the terminal end 126 of the lower section 103 of the elongated body 101, as shown in FIGS. 5A and 5B. Driving the lifting block 122 upward in the first axial direction A by rotating the inner rod 106 in the first clockwise or counterclockwise direction Q causes the foldable wings 110 to collapse into a folded configuration and assume the "deployed" position, as shown in FIG. 5A. Similarly, driving the lifting block 122 downward in the opposite second axial direction B by rotating the inner rod 106 in the opposite second clockwise or counterclockwise direction R causes the foldable wings 110 to straighten and assume the "non-deployed" position, as shown in FIG. 5B. In some embodiments, the inner threading 127 of the terminal end 126 is configured for engagement with the threaded portion 124 of the inner rod 106. This configuration of the inner threading 127 and the inner rod 106 allows a user to drive the inner rod 106 upward in the first axial direction A by rotating the inner rod 106 in the first clockwise or counterclockwise direction Q or to drive the inner rod 106 downward in the second axial direction B by rotating the inner rod 106 in the opposite second clockwise or counterclockwise direction R causes the foldable wings 110 to assume either the "non-deployed" or "deployed" positions. The anchor apparatus 100 can be locked in the "deployed" position by rotating the inner rod 106 in the first clockwise or counterclockwise direction Q within the terminal end 126 such that the inner rod 106 is tightened within the inner threading 127 and cannot be rotated any further in the first clockwise or counterclockwise direction Q. Similarly, the anchor apparatus 100 can be locked in the "non-deployed" position by rotating the inner rod 106 in the opposite second clockwise or counterclockwise direction R within the terminal end 126 such that the inner rod 106 is tightened within the inner threading 127 and cannot be rotated any further in the opposite second clockwise or counterclockwise direction R. In some embodiments, a lower end of the inner rod 106 includes a receptacle (not shown) for engagement with a handle 140 or a winch attachment (not shown).

Figures 4A, 4B, 4C:
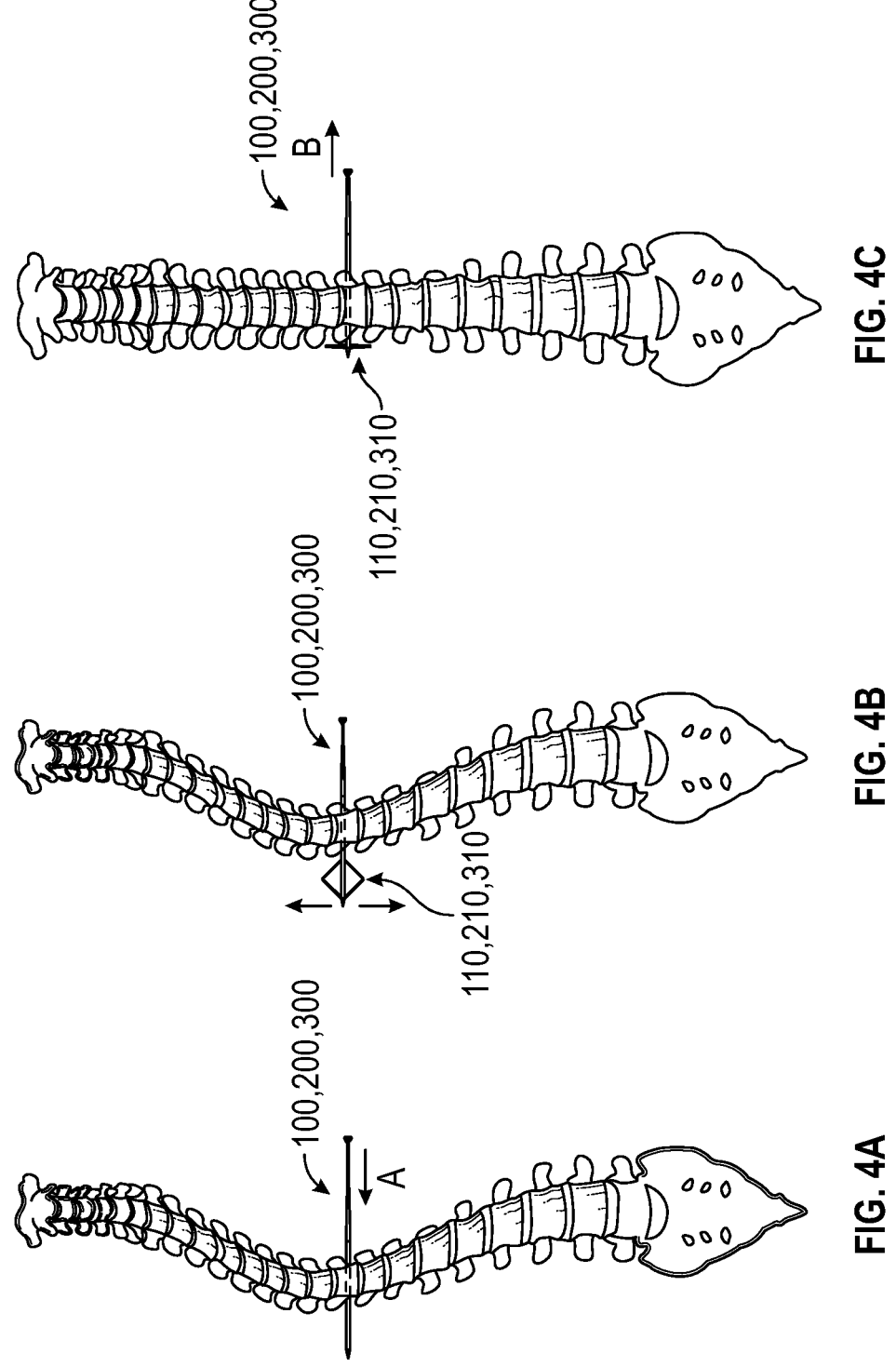
FIGS. 4A-4C are frontal views of the anchor apparatus of FIG. 1 illustrating sequential operation of the anchor apparatus during surgical realignment of a misaligned spine.

In one method of use of the anchor apparatus 100 shown in FIGS. 4A-4C, the head 105 of the anchor apparatus 100 is inserted between the vertebrae while in the non-deployed position and driven in a first axial direction A until the foldable wings 110 are positioned completely past the vertebrae. The foldable wings 110 are then folded into the deployed position by rotating the inner rod 106 in the first clockwise or counterclockwise direction Q such that the lifting block 122 drives the lower wing portion 112 in the first axial direction A, thereby causing the lower wing portion 112 to fold against the upper wing portion 111 in the deployed position. After the foldable wings 110 are properly deployed, a surgeon may manually pull on the handle 140 or use a winch with a winch attachment connected to the lower end of the inner rod 106 to pull the anchor apparatus in one direction 100 and, consequently, straighten into place the spine engaged with the anchor apparatus 100. In some embodiments, an intradiscal implant 400 may be used in conjunction with the anchor apparatus 100 to aid with accessing and engaging the intradiscal space.

Figure 15:
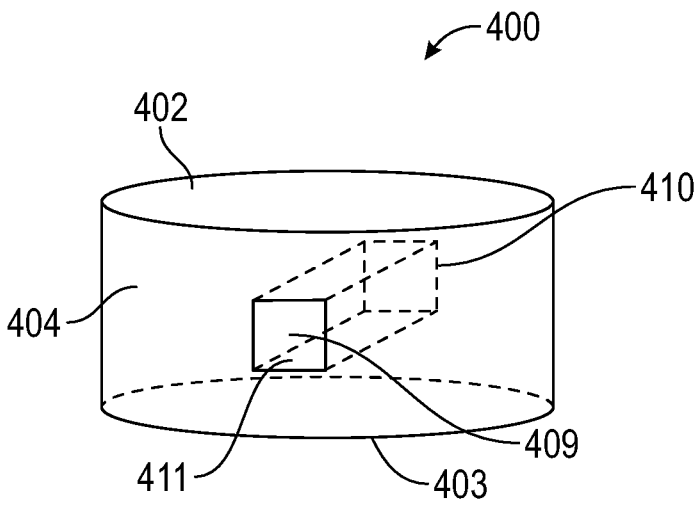
FIG. 15 is a perspective view of a first embodiment of an intradiscal implant having a channel for insertion of the anchor apparatuses of FIGS. 1 and 7.

Whenever a surgeon deems appropriate, the intradiscal implant 400 may be implanted into the spine to provide bone graft material and guiding structure for joint fusion. As shown in FIG. 15, the intradiscal implant 400 defines an upper face 402, a lower face 403, an outer surface 404 and a channel 409 that extends entirely through the intradiscal implant 400. In some embodiments, the intradiscal implant 400 defines a circular configuration, but is not limited to this shape and in some embodiments may be of a rectangular configuration. In some embodiments, the outer surface 404 defines an entrance aperture 410 in communication with the channel 409 at one end and an exit aperture 411 in communication with the channel 409 at an opposite thereof to facilitate insertion of the anchor apparatus 100 through the channel 409. In this configuration, the intradiscal implant 400 can be inserted between vertebrae and the anchor apparatus 100 along the axial direction A through the entrance aperture 410 of the channel 409. In operation, the foldable wings 110 are deployed and the lower wing portion 112 of each of the foldable wings 110 contacts the vertebrae and is pulled in the opposite axial direction B such that the misaligned spine becomes aligned. In some embodiments, the intradiscal implant 400 is installed by hammering the intradiscal implant 400 between the vertebrae from a concave side or a convex side of the misaligned spine. The anchor apparatus 200 is then inserted through the channel 409 of the intradiscal implant 400 and the foldable wings 110 deployed such that the lower wing portion 112 of each of the foldable wings 110 contacts the vertebrae, as shown sequentially in FIGS. 1A-18C. In some embodiments, the intradiscal implant 400 may define a plurality of additional channels (not shown) for receiving bone graft material for fusion of the vertebrae. Following the permanent installation of the intradiscal implant 400 and fixation of the spine using the anchor apparatus 100, one or more securing members (not shown) may be installed within the vertebrae and around the intradiscal implant 400 such that the vertebrae become fixated.

Figures 7, 8, 9:
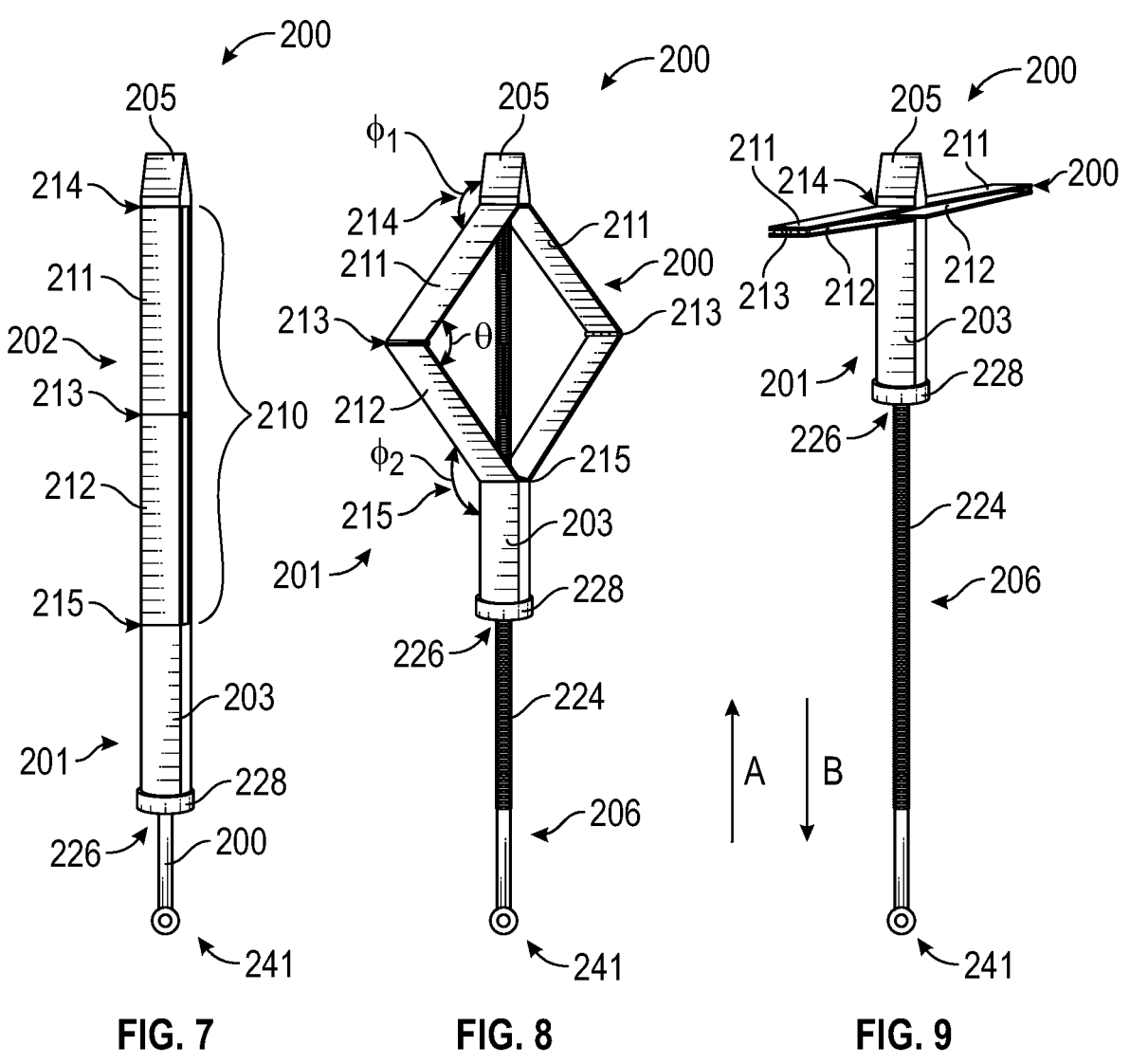
FIG. 7 is a perspective view of a second embodiment of the anchor apparatus for realignment of a misaligned spine in a "non-deployed" position.
FIG. 8 is a perspective view of the anchor apparatus of FIG. 7 for realignment of a misaligned spine in a "deploying" position.
FIG. 9 is a perspective view of the anchor apparatus of FIG. 7 for realignment of a misaligned spine in a "deployed" position.

A second embodiment of the anchor apparatus, designated 200 is shown in FIGS. 7-10. The general sequential operation of the anchor apparatus 100 shown in FIGS. 4A-4C also applies to the anchor apparatus 200. The anchor apparatus 200 includes an elongated body 201 defining an upper section 202 and a lower section 203 with the upper section 202 defining a head 205 and a pair of foldable wings 210, wherein the pair of foldable wings 210 can be deployed by driving the lower section 203 of the elongated body 201 in a first axial direction A or an opposite second axial direction B such that the foldable wings 210 of the elongated body 201 collapse into an "anchor" shape shown in FIG. 9. The anchor apparatus 200 further includes an inner rod 206 to maintain rigidity during deployment of the foldable wings 210 that includes a locking mechanism 220 operable for locking the anchor apparatus 200 in a "non-deployed" position (FIG. 7) or a "deployed" position (FIG. 9). An intermediate "deploying" position is further illustrated in FIG. 8. In the deployed position, a lateral extension profile of the anchor apparatus 200 is expanded. Conversely, in the non-deployed position, the lateral extension profile of the anchor apparatus 200 is minimized.

In some embodiments, the elongated body 201 may be broadly defined as a square or cylindrical rod shape defining the upper section 202 and the lower section 203. As discussed above, the elongated body 201 includes the pair of foldable wings 210 which, when in the "non-deployed"

position, form part of the upper section 202 of the elongated body 201. In some embodiments shown in FIG. 10, threaded portion 213 of the inner rod 212 engages with an inner threading 229 of the nut 228. The inner rod 206 is disposed within a channel 204 defined by the lower section 203. In some embodiments, the nut 228 is tall enough for a user to comfortably grip with the fingers of a user such that the nut 228 may be manually rotated in a clockwise or counterclockwise direction Q and the lower section 203 of the elongated body 201 can then be driven in an axial direction A towards the head 205. This operation causes the foldable wings 210 of the anchor apparatus 200 to fold and assume the "deployed" position of FIG. 9. Similarly, rotating the nut 228 in an opposite clockwise or counter-clockwise direction R drives the lower section 203 of the elongated body 201 in an axial direction B away from the head 205 such that the foldable wings 210 straighten and assume the "non-deployed" position of FIG. 7.

In some embodiments of the anchor apparatus 200, each pair of foldable wings 210 forms part of the upper section 202 of the elongated body 201. In particular, each pair of foldable wings 210 defines an upper wing portion 211 and a lower wing portion 212, wherein a proximal end of the upper wing portion 211 and a distal end of the lower wing portion 212 are joined together using a middle joint 213. Using FIGS. 6A-6C as a reference, the middle joint 213 allows one rotational degree of freedom to define a main angle θ between the upper wing portion 213 and the lower wing portion 212. The upper wing portion 211 is joined to the head 205 of the elongated body 201 by an upper joint 214. The upper joint 214 also allows one rotational degree of freedom to define an upper angle $\phi_1$ between the upper wing portion 211 of the foldable wing 210 and the head 205 of the elongated body 201. The lower wing portion 212 is joined to the lower section 203 of the elongated body 201 by a lower joint 215, wherein the lower joint 215 allows one rotational degree of freedom to define a lower angle $\phi_2$ between the lower wing portion 212 of the foldable wing 210 and lower section 203 of the elongated body 210. As shown in FIG. 6A, while in the non-deployed position, all three angles $\phi_1$, θ, and $\phi_2$ are about 180°. Conversely, as shown in FIG. 6C, while in the deployed position, the upper and lower angles $\phi_1$, and $\phi_2$ are about 90° and the main angle θ is close to 0°. A view of the angles $\phi_1$, θ, and $\phi_2$ in the intermediate "deploying" position is shown in FIG. 6B. In one aspect, the upper, middle, and lower joints 214, 213 and 215 may be a mechanical hinge or a bendable material. In some embodiments, the hinge or bendable material is tensioned such that a resting position of the hinge or bendable material is straightened to provide tactile feedback when bending the upper, middle and lower joints 214, 213 and 215.

Figure 10:
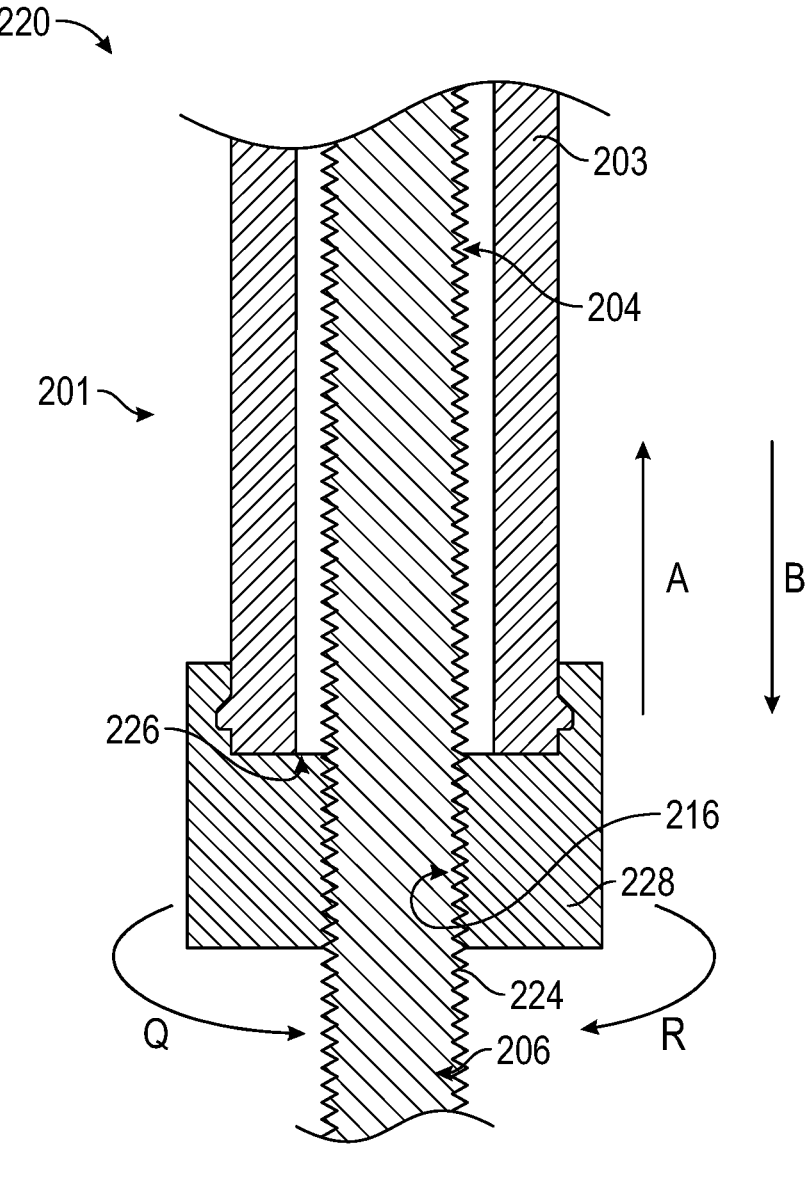
FIG. 10 is a cross-sectional view of a locking mechanism of the anchor apparatus of FIG. 7 showing an inner rod engaged with a rotatable nut for transitioning between the "non-deployed" and "deployed" positions.

A locking mechanism 220 of the anchor apparatus 200 is shown in FIG. 10 in which the lower section 203 of the elongated body 201 defines a terminal end 226. In some embodiments, the terminal end 226 of the lower section 203 is engaged with the nut 228 that is operable for rotation around the inner rod 206 such that the lower section 203 follows the vertical motion of the nut 228. As shown in FIG. 10, an inner threading 229 of the nut 228 is engaged with the threaded portion 224 of the inner rod 206 such that when the nut 228 is rotated in a first clockwise or counterclockwise direction Q or an opposite second clockwise or counterclockwise direction R, the lower section 203 is driven in either the first axial direction A or the second axial direction B, respectively. As discussed above, the inner rod 206 is disposed within the channel 204 defined by the lower section 203.

The collapsibility of the pair of foldable wings 210 is made possible by the operative co-operation between the lower section 203, the nut 228 and the inner rod 206. In some embodiments, an upper end 208 of the inner rod 206 is connected with an underside of the head 205 and is disposed through the channel 204 of the lower section 203 of the elongated body 201. Furthermore, the inner rod 206 is engaged with the nut 228 located at the terminal end 226 of the lower section 203, as shown in FIG. 10. Driving the lower section 203 upward in the first axial direction A causes the foldable wings 210 to fold and assume the "deployed" position, as shown in FIG. 9. Similarly, driving the lower section 203 downward in the opposite second axial direction B causes the foldable wings 210 to straighten and assume the "non-deployed" position, as shown in FIG. 7. In some embodiments, the inner threading 229 of the nut 228 is operable to engage the threaded portion 224 of the inner rod 206. This configuration of the lower section 203, the nut 228 and the inner rod 206 allows a user to drive the lower section 203 upward in the first axial direction A by rotating the nut 228 around the inner rod 206 in the first clockwise or counterclockwise direction Q to configure the foldable wings 210 of the anchor apparatus 200 into the "deployed" position. Likewise, a user can drive the lower section 203 downward in the second axial direction B by rotating the nut 228 in the opposite second clockwise or counterclockwise direction R to configure the foldable wings 210 of the anchor apparatus 200 into the "non-deployed" position. The anchor apparatus 200 can be locked in the "deployed" position by rotating the nut 228 in the first clockwise or counterclockwise direction Q around the inner rod 206 such that the nut 228 is tightened around the threaded portion 224 of the inner rod 206 and cannot be rotated any further in the first clockwise or counterclockwise direction Q. In addition, the anchor apparatus 200 can be locked in the "non-deployed" position by rotating the nut 228 in the opposite second clockwise or counterclockwise direction R around the inner rod 206 such that the nut 228 is tightened around the threaded portion 224 of the inner rod 206 and cannot be rotated any further in the opposite second clockwise or counterclockwise direction R. In some embodiments, a lower end 207 of the inner rod 206 includes a receptacle (not shown) for engagement with a handle (not shown) or a winch attachment 241.

In one method of use of the anchor apparatus 200 shown in FIGS. 4A-4C, the anchor apparatus 200 is inserted point-first between vertebrae while in the non-deployed position and is driven in a first axial direction A until the foldable wings 210 are positioned completely past the vertebrae. The foldable wings 210 are then folded into the deployed position by rotating the nut 228 in the first clockwise or counterclockwise direction Q such that the lower section 203 drives the lower wing portion 212 in the first axial direction A, thereby causing the lower wing portion 212 to fold against the upper wing portion 211 in the deployed position. After the foldable wings 210 are properly deployed, a surgeon may pull on the handle 240 or use a winch with a winch attachment connected to the lower end of the inner rod 206 to pull the anchor apparatus 200 in the opposite axial direction B and consequently straighten in place the spine engaged with the anchor apparatus 200 into place. In some embodiments, the intradiscal implant 400 may be used in conjunction with the anchor apparatus 200 to aid with accessing and engaging the intradiscal space.

A third embodiment of the anchor apparatus, designated 300, is shown in FIGS. 11-14B. The general sequential operation of the anchor apparatus 100 and 200 shown in FIGS. 4A-4C and 6A-6B also applies to the operations of the anchor apparatus 300. The anchor apparatus 300 includes an elongated body 301 defining an upper section 302 and a lower section 303, the upper section 302 defining a head 305 and a pair of foldable wings 310, wherein the pair of foldable wings 310 can be deployed by driving the lower section 303 of the elongated body 301 in a first axial direction A or an opposite second axial direction B such that the foldable wings 310 of the elongated body 301 form an "anchor" shape shown in FIG. 13. The anchor apparatus 300 further includes an inner rod 306 to maintain rigidity during deployment and a locking mechanism 320 operative for locking the anchor apparatus in a "non-deployed" position (FIG. 11) or a "deployed" position (FIG. 13). An intermediate "deploying" position is further illustrated in FIG. 12. In the deployed position, a lateral extension profile of the anchor apparatus 300 is expanded. Conversely, in the non-deployed position, the lateral extension profile of the anchor apparatus 300 is minimized.

In some embodiments, the elongated body 301 may be broadly defined as a square or cylindrical rod shape defining the upper section 302 and the lower section 303. As discussed above, the elongated body 301 includes the pair of foldable wings 310 which, when in the "non-deployed" position, form part of the upper section 302 of the elongated body 301 such that the elongated body 301 is one elongated piece. In some embodiments shown in FIGS. 12 and 13, the inner rod 306 defines most of the elongated body 301. A runner 322 is formed around the inner rod 306 and is configured to be driven in a first axial direction A or an opposite second axial direction B. The runner 322 is engaged with the pair of foldable wings 310 such that when the runner 322 is driven in the first axial direction A, the pair of foldable wings 310 assumes the deployed position shown in FIG. 13. Similarly, when the runner 322 is driven in the opposite second axial direction B, the pair of foldable wings 310 folds and assumes the non-deployed position of FIG. 11.

In some embodiments of the anchor apparatus 300, each pair of foldable wings 310 forms part of the upper section 302 of the elongated body 301. In particular, each of the pair of foldable wings 310 defines an upper wing portion 311 and a lower wing portion 312, wherein a proximal end of the upper wing portion 311 and a distal end of the lower wing portion 312 are joined together using a middle joint 313. Similar to the embodiment shown in FIGS. 6A-6C where the middle joint 313 allows one rotational degree of freedom to define a main angle $\theta$ between the upper wing portion 313 and the lower wing portion 312. The upper wing portion 311 is joined to the head 305 of the elongated body 301 by an upper joint 314. The upper joint 314 allows one rotational degree of freedom to define an upper angle $\phi_1$ between the upper wing portion 311 of the foldable wing 310 and the head 305 of the elongated body 301. Similarly, the lower wing portion 312 is joined to the runner 322 by a lower joint 315, wherein the lower joint 315 allows one rotational degree of freedom to define a lower angle $\phi_2$ between the lower wing portion 312 of the foldable wing 310 and lower section 303 of the elongated body 310. In some embodiments shown in FIGS. 12 and 13, a spring 331 is included between the runner 322 and the head 305 to provide tension against the runner 322 while the foldable wings 310 are locked in the "deployed" position such that an axial force is applied to the runner 322 in the opposite second axial direction B.

A locking mechanism 320 for the anchor apparatus 300 is shown in FIGS. 14A and 14B. In some embodiments, an upper fin lock 327 (FIG. 14B) may be shaped like a fin having a curved edge 328 and a flat edge 329 protruding from an upper fin aperture 324 defined by the inner rod 306. The upper fin lock 327 is engaged with an upper fin spring 325 which applies a lateral force to the upper fin lock 327 in a first lateral direction E. The runner 322 is able to slide over the curved edge 328 and force the upper fin lock 327 into the inner rod 306 when being driven in the first axial direction A. Once the runner 322 has passed over the upper fin lock 327, the upper fin lock 327 is forced outward again by the upper fin spring 325, locking the runner 322 in position beyond the flat edge 329. The axial force applied to the runner 322 by the spring 331 in the opposite second axial direction B ensures that the runner 322 remains in contact with the flat edge 329 while in the "deployed" position. The upper fin lock 327 can be unlocked by manually pushing the upper fin lock 327 into the upper fin aperture 324 in the opposite second lateral direction F such that the runner 322 is driven over the upper fin lock 327 in the opposite second axial direction B.

Similarly, the runner 322 will slide over a curved edge 338 of a lower fin lock 337 (FIG. 14A) and push the lower fin lock 337 into a lower fin aperture 334 while traveling in the opposite axial direction B and will become locked beyond a flat edge 339. The lower fin lock 337 is engaged with a lower fin spring 335 which applies a lateral force to the lower fin lock 337 in a first lateral direction E. The locking mechanism 320 can be unlocked by manually pushing a button 323 defined on a surface of the runner 322 such that the button 323 pushes the lower fin lock 337 into the lower fin aperture 334 in the opposite second lateral direction F. such that the runner 322 is driven over the lower fin lock 337 in the first axial direction B. In this manner, the anchor apparatus 300 is able to lock between the "closed" and "deployed" positions.

The collapsibility of the pair of foldable wings 310 are made possible by the operative co-operation of the lower section 303, the runner 322 and the inner rod 306. In some embodiments, an upper end of the inner rod 306 is connected with an underside of the head 305 and forms the majority of the elongated body 301. Furthermore, the inner rod 306 is engaged with the runner 322 such that the runner 322 may be driven in the first axial direction A or the opposite second axial direction B, as shown in FIGS. 11-13. Driving the runner 322 upward in the first axial direction A causes the foldable wings 310 to collapse and assume the "deployed" position, as shown in FIG. 13. Similarly, driving the runner 322 downward in the opposite second axial direction B causes the foldable wings 310 to straighten and assume the "non-deployed" position, as shown in FIG. 11. In some embodiments, a lower end 307 of the inner rod 307 includes a receptacle (not shown) for engagement with a handle (not shown) or a winch attachment 341.

In one method of use of the anchor 300 shown in FIGS. 4A-4C, the anchor apparatus 300 is inserted point-first between vertebrae while in the non-deployed position and is driven in a first axial direction A until the foldable wings 310 are positioned completely past the vertebrae. The foldable wings 310 are then folded into the deployed position by driving the runner 322 in the first axial direction A such that the lower wing portion 312 is similarly driven in the first axial direction A, thereby causing the lower wing portion 312 to fold against the upper wing portion 311 in the deployed position. After the foldable wings 310 are properly deployed, a surgeon may pull on the handle (not shown) or use a winch with a winch attachment 341 connected to the lower end of the inner rod 306 to pull the anchor apparatus 300 in the opposite axial direction B and consequently straighten in place the spine engaged with the anchor apparatus 300. In some embodiments, an intradiscal implant 500 may be used in conjunction with the anchor apparatus 300 to aid with accessing and engaging the intradiscal space.

Figure 16:
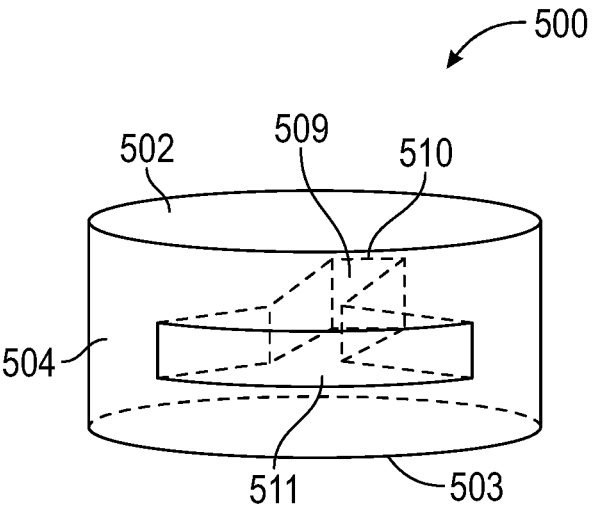
FIG. 16 is a perspective view of a second embodiment of the intradiscal implant having a channel for insertion of the anchor apparatus of FIG. 11.
Figures 17A, 17B:
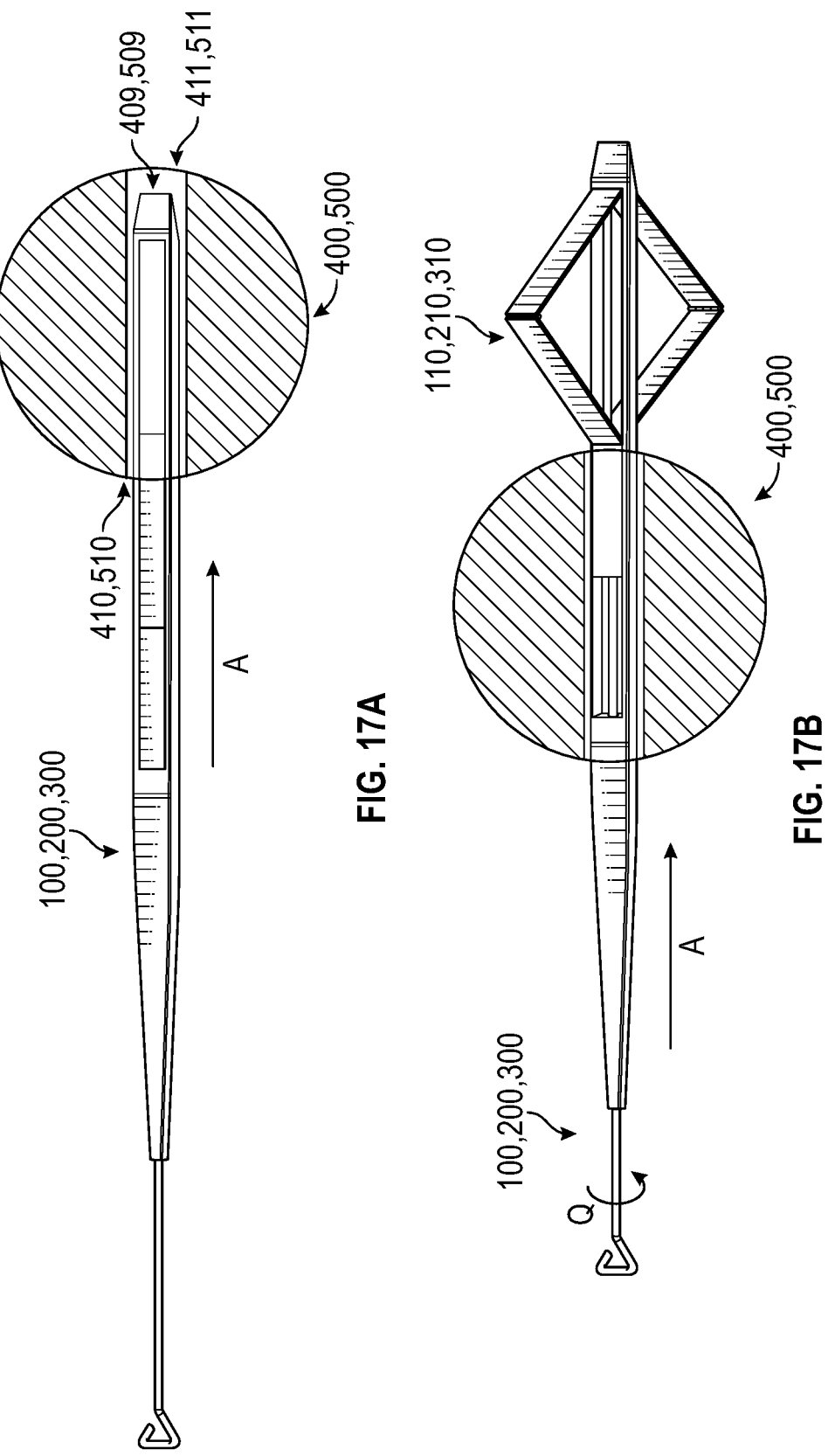
FIGS. 17A-17C are cross-sectional views of the anchor apparatus of FIG. 1, and applicable to the anchor apparatuses of FIGS. 7 and 11 illustrating sequential operation of the anchor apparatus within the corresponding intradiscal implant of FIG. 15, also applicable to the intradiscal implant of FIG. 16.
Figure 17C:
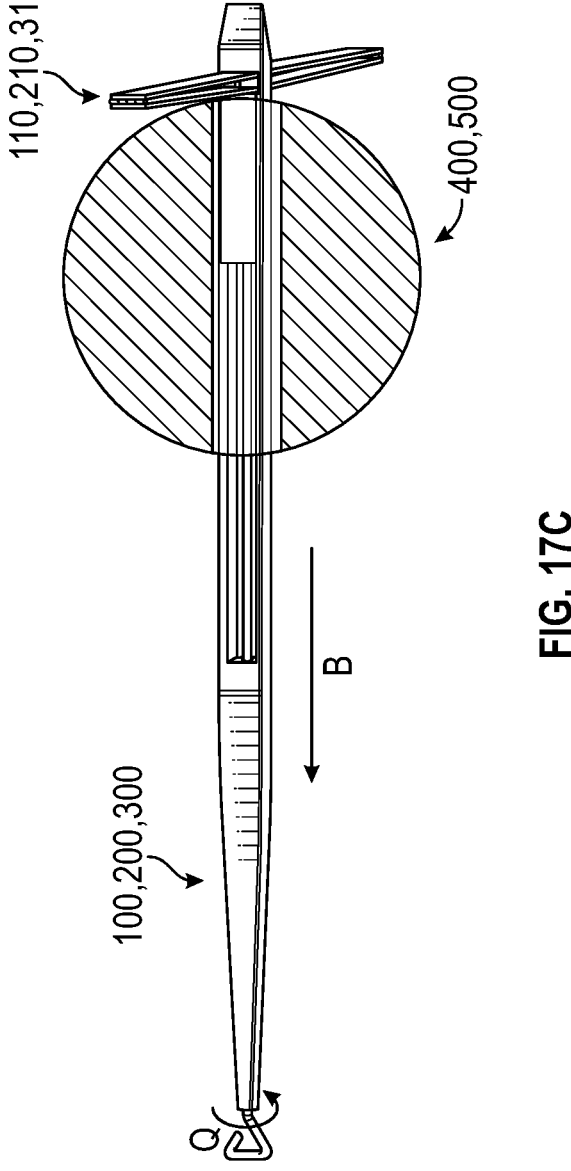
Figure 18A:
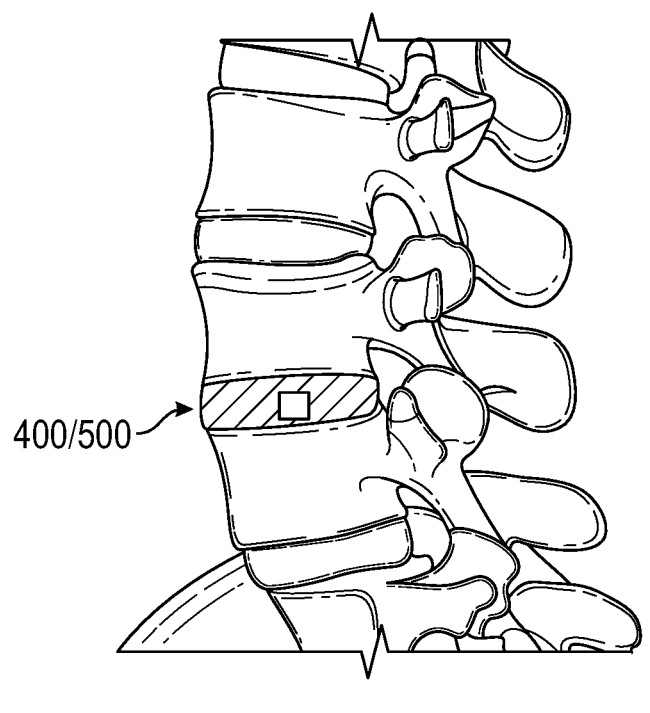
FIGS. 18A-18C are top views of the anchor apparatus of FIG. 1, and applicable to the anchor apparatuses of FIGS. 7 and 11 illustrating sequential operation of the anchor apparatus within the corresponding intradiscal implant of FIG. 15, also applicable to the intradiscal implant of FIG. 16, where the intradiscal implant is installed between vertebrae.
Figure 18B:
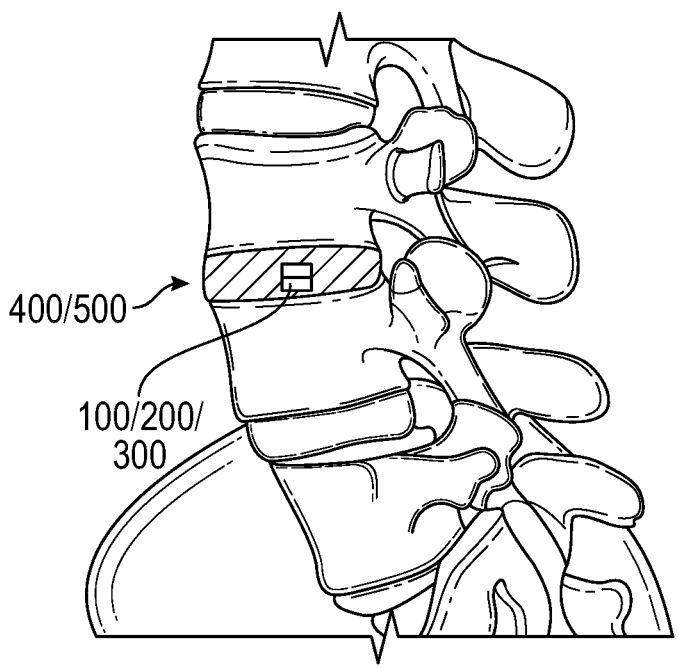
Figure 18C:
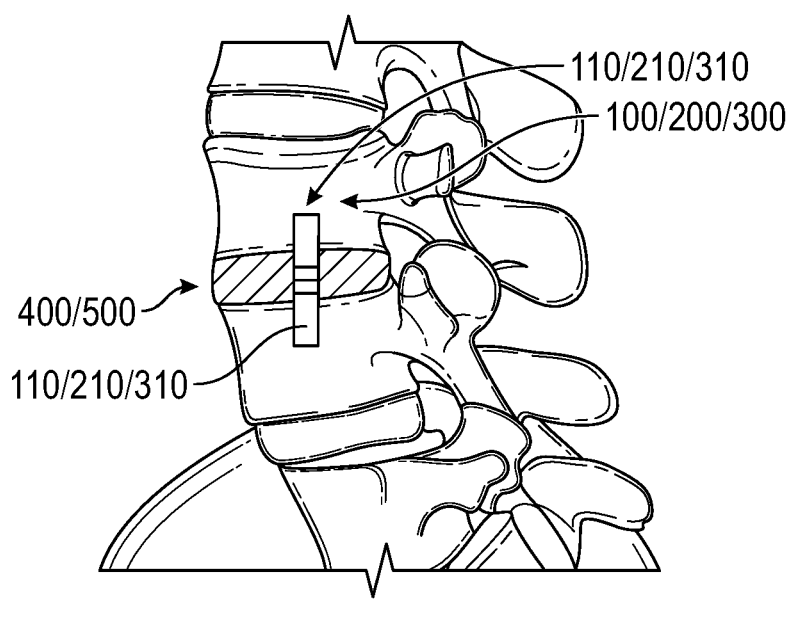

Referring to FIG. 16, in some embodiments the intradiscal implant, designated as 500, defines an upper face 502, a lower face 503, a outer surface 504 and a channel 509 that extends entirely through the intradiscal implant 500. In some embodiments, the intradiscal implant 500 defines a circular configuration, but is not limited to this shape and in some embodiments may be of a rectangular configuration. In some embodiments, the outer surface 504 defines an entrance aperture 510 in communication with one end of the channel 509 and an exit aperture 511 in communication with an opposite end of the channel 509 to facilitate insertion of the anchor apparatus 300 through the channel 509. The intradiscal implant 500 is meant to be used with the anchor apparatus 300 and thus, the exit aperture 511 of the channel 509 is formed wider than the entrance aperture 510 to support the foldable wings 310 while the anchor apparatus 300 is being pulled in the second axial direction B. In this manner, the intradiscal implant 500 can be inserted between vertebrae and the anchor apparatus 300 may be inserted in the axial direction A through the entrance aperture 510 of the channel 509. In operation, the foldable wings 310 are deployed such that the lower wing portion 312 of each of the foldable wings 310 contacts the outer surface 504 and pulled in the opposite axial direction B that causes the misaligned spine to be aligned. In some embodiments, the intradiscal implant 500 is installed by hammering the intradiscal implant 500 between the vertebrae from a concave side or a convex side of the misaligned spine. The anchor apparatus 300 is then inserted through the channel 509 and the foldable wings 310 are deployed such that the lower wing portion 312 of each of the foldable wings 310 contacts the vertebrae, as shown sequentially in FIGS. 17A-18C. Securing members (not shown) may be installed within the vertebrae and around the intradiscal implant 500 such that the vertebrae are fixated. In some embodiments, the intradiscal implant 500 may define a plurality of additional channels (not shown) for receiving bone graft material for fusion of the vertebrae. Following the installation of the intradiscal implant 500 and fixation of the spine using the anchor apparatus 300, the intradiscal implant 500 may installed between the vertebrae.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A device for spinal realignment, comprising:
an anchor apparatus configurable in a non-deployed configuration and a deployed configuration, comprising:
an elongated body defining a first section, a second section, and a channel extending axially through the elongated body wherein the second section is positionable within an intradiscal space of a spinal column and wherein the first section includes a pair of deployable wings defined by the first section, each deployable wing of the pair of deployable wings comprising a first portion pivotably engaged with a second portion by a middle joint, wherein the first portion is pivotably engaged with the first section of the elongated body by a first joint and wherein the second portion is pivotably and slidably engaged with the channel of the elongated body by a second joint; and an inner rod disposed within the channel in operative association with the second joint of each deployable wing of the pair of deployable wings and configured to transition the anchor apparatus between a non-deployed position and a deployed position by actuating the second joint along a direction of elongation of the channel; and wherein, when deployed beyond the intradiscal space, the second portion of each deployable wing bears against a contralateral side of a vertebral body and, upon application of a proximally-directed axial pulling force along a longitudinal axis of the elongated body to the second section from an ipsilateral side of the vertebral body, the force is reacted at the contralateral side of the vertebral body via the pair of deployable wings, wherein the second section of the elongated body extends from the ipsilateral side of the vertebral body.

2. The device of claim 1, wherein rotating the inner rod in a first rotational direction about the direction of elongation of the channel drives the second portion of each deployable wing in a first axial direction relative to the first portion such that the second portion and the first portion of each deployable wing assumes the deployed position.

3. The device of claim 2, wherein rotating the inner rod in an opposite second rotational direction about the direction of elongation of the channel drives the second portion of each of the pair of deployable wings in an opposite second axial direction relative to the first portion such that the second portion and the first portion of the pair of deployable wings assume the non-deployed position.

4. The device of claim 1, wherein the elongated body further comprises a head defined by the first section.

5. The device of claim 1, further comprising:

a lifting block defined by the second section of the elongated body at a first end of the inner rod;

wherein the second portion of each of the deployable wings is engaged with the lifting block by the second joint.

6. The device of claim 5 further comprising:

a locking mechanism for locking the anchor apparatus in the deployed position or the non-deployed position, the locking mechanism defined by the second section, the locking mechanism including:

a terminal end collectively defined by the second section of the elongated body and the channel, wherein the channel of the elongated body terminates in an inner threading defined by the terminal end of the elongated body; and a threaded portion defined by the inner rod and engaged with the inner threading of the terminal end of the elongated body.

7. The device of claim 6, wherein the inner rod and the terminal end of the locking mechanism assume a locked position when the pair of deployable wings is in the deployed position or non-deployed position.

8. The device of claim 5, wherein the channel defines a pair of tracks located lateral to the channel and wherein each of the pair of tracks defines a grooved surface and wherein the lifting block is engaged with the grooved surface of the channel such that the lifting block cannot be disengaged from the channel.

9. The anchor of apparatus claim 1, wherein the locking mechanism comprises:

a nut defining an inner threading and engaged with a terminal end of the lower section of the elongated body, wherein the nut is operable for rotating independently of the lower section; and a threaded portion defined by the inner rod and engaged with the inner threading of the nut;

wherein rotating the nut in a first clockwise or counterclockwise direction drives the lower section of the elongated body in a first axial direction until the pair of deployable wings assume the deployed position; and wherein rotating the nut in a second opposite clockwise or counterclockwise direction drives the lower section of the elongated body in an opposite second axial direction until the pair of deployable wings assume the non-deployed position.

10. The anchor apparatus of claim 9, wherein the inner rod and nut assume a locked position when the pair of deployable wings is in the deployed position or the non-deployed position.

11. The anchor apparatus of claim 1, wherein the locking mechanism comprises:

a runner formed by the lower section of the elongated body, wherein the inner rod is disposed through the runner and wherein the runner is configured to be driven in a first axial direction or an opposite second axial direction;

an upper fin protruding from an upper fin aperture defined by the inner rod, wherein an upper fin spring disposed inside the inner rod applies a lateral force in a first lateral direction to the upper fin; and a lower fin protruding from a lower fin aperture defined by the inner rod, wherein a lower fin spring located inside the inner rod applies a lateral force in the first lateral direction to the lower fin;

wherein driving the lower section of the elongated body in a first axial direction until the pair of deployable wings assume the deployed position causes the runner to ride over a curved side of the upper fin and become engaged with a flat side of the upper fin such that the lower section assumes a locked position and cannot be driven in the opposite second axial direction;

wherein driving the lower section of the elongated body in the opposite second axial direction until the pair of deployable wings assume the non-deployed position causes the runner to ride over a curved side of the lower fin and become engaged with a flat side of the lower fin such that the lower section assumes a locked position and cannot be driven in the first axial direction.

12. The anchor apparatus of claim 11, wherein pushing the upper fin or the lower fin in an opposite second lateral direction into the inner rod causes the runner to assume an unlocked position such that the runner can be driven in the first axial direction or the second axial direction, and wherein the lower fin can be pushed into the lower fin aperture using a button defined on the runner.

13. The anchor apparatus of claim 11, wherein the upper portion of each of the pair of deployable wings is tensioned while in the deployed position such that an axial force is applied to the lower portion in the second axial direction by the upper portion of the pair of deployable wings.

14. The anchor apparatus of claim 13, wherein an axial force is applied to the runner in the second axial direction by the lower portion of the pair of deployable wings such that the runner contacts the flat side of the upper fin in the locked position.

15. The device of claim 1, wherein a second end of the inner rod is configured for engagement with a handle.

16. The device of claim 15, further comprising a winch attachment configured for engagement with the second end of the inner rod for applying the proximally-directed axial pulling force to the second section of the elongated body from the ipsilateral side of the vertebral body.

\* \* \* \* \*